US005540697A

United States Patent [19]
Rehmann et al.

[11] Patent Number: 5,540,697
[45] Date of Patent: Jul. 30, 1996

[54] PROSTHETIC SOCKET INSTALLATION APPARATUS AND METHOD

[75] Inventors: Mark L. Rehmann, Pflugerville; Steven I. Whitlock, Austin, both of Tex.

[73] Assignee: U.S. Medical Products, Inc., Austin, Tex.

[21] Appl. No.: 321,064

[22] Filed: Oct. 7, 1994

Related U.S. Application Data

[63] Continuation-in-part of Ser. No. 17,141, Feb. 12, 1993, abandoned.

[51] Int. Cl.$^6$ ............................ A61B 17/92; A61B 17/88
[52] U.S. Cl. ........................... 606/91; 606/100; 294/95
[58] Field of Search ........................... 623/22; 606/99, 606/91, 100, 79, 86, 87, 89; 294/95

[56] References Cited

U.S. PATENT DOCUMENTS

| | | | |
|---|---|---|---|
| 3,036,482 | 5/1962 | Kenworthy | 606/100 X |
| 3,587,115 | 6/1971 | Shiley | 623/2 |
| 3,605,123 | 9/1971 | Hahn . | |
| 4,290,638 | 9/1981 | Manning | 294/95 X |
| 4,305,394 | 12/1981 | Bertuch | 606/91 |
| 4,549,319 | 10/1985 | Meyer | 623/22 |
| 4,577,899 | 3/1986 | Hemingway | 294/95 |
| 5,059,196 | 10/1991 | Coates | 606/99 |
| 5,116,339 | 5/1992 | Glock | 606/91 |
| 5,141,512 | 8/1992 | Farmer et al. | 606/87 |
| 5,169,399 | 12/1992 | Ryland et al. | 606/91 |
| 5,171,243 | 12/1992 | Kashuba et al. | 606/86 |
| 5,171,313 | 12/1992 | Salyer | 606/86 |

FOREIGN PATENT DOCUMENTS

| | | | |
|---|---|---|---|
| 0327509 | 8/1989 | European Pat. Off. | 623/22 |
| 470912 | 2/1992 | European Pat. Off. | 606/99 |
| 2119206 | 10/1972 | Germany | 294/95 |
| 52-61050 | 5/1977 | Japan | 294/95 |
| 0779267 | 11/1980 | U.S.S.R. | 294/95 |
| 1507368 | 9/1989 | U.S.S.R. | 623/2 |
| 8605679 | 10/1986 | WIPO | 623/18 |

OTHER PUBLICATIONS

Fiber Metal Biologic Implant Fixation, Current Topics in Orthopaedic Technology vol. 1, No. 3.
IOI, Jan. 1990, 1000–01–158, pp. 17–19, Surgical Technique Protocal.
Osteonics, Surgical Protocall Omnifit, PSL Cemented Application, pp. 12, 16 Surgical Technique Protocall.
Johnson & Johnson #OT–200, 1991, Seating of the Permanent Acetabular Prosthesis.
BioPro PSL Brochure, Acetabular Remolding and Implantation, p. 4.

*Primary Examiner*—David H. Willse
*Attorney, Agent, or Firm*—Russell D. Culbertson; Shaffer & Culbertson

[57] ABSTRACT

A prosthetic socket implant installation apparatus and method combines holding, impacting, and aligning functions in a modular device. The apparatus comprises an installation tool that firmly engages a feature around the inner rim of a prosthetic socket implant so that the shell does not disengage during the installation process. An implant engaging arrangement on the installation tool is capable of extending to properly engage and hold implants in a broad range of sizes. The tool provides both axial and angular alignment references to facilitate the correct alignment of a prosthetic socket implant during installation. A mechanically isolated impacting rod slideably attaches within an opening along the longitudinal axis of the tool thus facilitating impact at the proper location and angle and allowing the alignment and impacting to be performed by one person. A method for installing a prosthetic socket implant includes retracting implant engaging means, engaging the socket, aligning the socket in the opening, installing the socket, and disengaging the socket.

7 Claims, 5 Drawing Sheets

PROSTHETIC SOCKET INSTALLATION APPARATUS AND METHOD

This is a continuation in part of application Ser. No. 08/017,141, filed Feb. 12, 1993 and now abandoned.

BACKGROUND OF THE INVENTION

This invention relates to total joint structure replacement and particularly to an apparatus and method for installing a prosthetic socket structure during complete ball-and-socket type joint replacement surgery.

Complete joint replacement may be required for ball-and-socket type joints when both the anatomic ball and the anatomic socket components of the joint structure have severely degraded or otherwise been damaged. The surgical replacement procedure, called arthroplasty, includes replacing both the natural anatomic ball or head of the joint and the natural anatomic socket structure with prosthetic components. The prosthetic ball structure includes a head adapted to replace the ball structure of the natural joint and the prosthetic socket structure provides a socket implant in which the prosthetic head articulates.

Complete hip joint replacement, for example, includes removing the anatomic ball structure by resecting the femoral head and neck of the femur and then securing the replacement prosthetic ball implant to the femur with a femoral stem prosthesis that is impacted deep into the proximal and intermedular canal of the femur. Replacing the socket structure includes removing the cartilage that lines the natural acetabulum or socket and perhaps some bone to leave a substantially hemispherical shaped opening or acetabular cavity in the pelvic bone for receiving the prosthetic socket implant. After producing the desired hemispherically shaped opening, the surgical procedure includes affixing the prosthetic socket structure in the opening by either pressing, impacting, or cementing the prosthetic implant into the acetabular cavity.

There are two general prosthetic socket implant types that replace the natural acetabulum of the hip joint. The first type is a one-piece implant structure constructed of polyethylene or other high grade plastic. The one-piece implant structure includes a socket for receiving the prosthetic ball and a generally hemispherical outer surface adapted to correspond to the opening made in the pelvic bone. Installing the one-piece socket design includes cementing the outer surface of the implant to the opening made in the pelvic bone.

The second type of acetabular socket prosthesis is a two piece structure. The first piece comprises a substantially hemispherical or cylindrical acetabular shell, typically constructed of a biologically compatible metal. The second piece comprises an insert that permanently attaches substantially within the acetabular shell and forms a prosthetic socket for receiving the prosthetic ball. The insert is typically constructed of an ultra high molecular weight polyethylene or other suitable plastic. Installing the two-piece prosthetic socket structure includes either pressing or impacting the acetabular shell into the pelvic bone, commonly referred to as a "press fit," or cementing the shell into the opening with polymethelmethacricate "PMMA" or other suitable bonding compound.

In the first step of installing the two-piece socket structure, the surgeon reams out the pelvic opening until cortical bone is exposed. The reamed acetabulum is then gaged to determine the proper size implant. In either the press fit or cementing procedure, surgeons use different sized trial shells to check the size of the opening. The trial shells are identical in shape to the actual shell to be installed but are smooth on their outer surfaces so as not to grip the bone and are larger or smaller than the shell to be installed depending upon the fixation technique to be employed. For receiving a press fit acetabular shell, the surgeon selects the prosthesis so that it is somewhat larger than the inner surface of the reamed acetabulum. When the surgeon presses or impacts the shell into place, the bone compresses tightly against the outer surface of the prosthetic shell to hold the shell in place. In the case of a cemented installation, the surgeon sizes the prosthetic implant somewhat smaller than the outer surface of the acetabular shell. The gap between the shell and the bone provides space for bone cement that bonds the shell to the bone.

The prosthetic socket must align properly in the pelvic opening to provide proper prosthetic function. The acetabular component must be aligned both axially and angularly within the pelvic bone. The axial alignment relates the angle of the centerline of the prosthesis with the pelvis. The angular alignment relates the prosthesis angular rotation with respect to the superior region of the natural acetabulum. Axial alignment of the acetabular prosthesis involves the commonly referenced angles of anteversion and abduction. Typically, the axial alignment should be within 5 degrees of the ideal axial alignment to provide satisfactory results. Surgeons often align the shells based upon experiences from past operations, but, less experienced surgeons may require a guide to correctly align the shell.

Most acetabular shells include holes through which bone screws may be secured into the pubis, ischium, and superior region of the pelvis. The bone screws provide immediate fixation for the acetabular shell in the prepared pelvic bone opening and reduce the possibility of prosthetic shifting or migration. The screw holes in the acetabular shell are angularly aligned with the pubis, ischium, and superior region of the pelvis. If the acetabular shell is improperly aligned either angularly or axially, one or more of the screws could accidentally extend completely through the pelvis and puncture an organ, requiring emergency surgery to repair the damage.

Prior devices for aligning and seating acetabular shells include holding devices, impacting devices, and combination holding and impacting devices. Holding devices attach to the prosthetic socket shells and allow surgeons to align the shells in the prepared opening. One device, the acetabular shell holder by Intermedics, Inc., grasped the rim of the shell but disengaged from the shell if excessively torqued. Therefore, the device could be used only to align the shell, and, because the handle of the device extended to the side of the tool, the device could not be used at all for any type of impaction. Further, because this device had to be used in conjunction with an impacting device during press-fit installations, the impacting process required a surgical assistant. Maintaining correct alignment during the impacting process was difficult due to the weak grip the instrument had on the rim of the shell.

One impacting device, the acetabular dome impactor by Biopro, included a round end that loosely engages the prosthetic shell and a handle that provided no axial alignment reference. However, because it did not firmly attach to the shell, the device provided no axial aligning force and no angular aligning support. Further, because the device was not fixed during the impacting process, misalignment during the impacting process was likely. Several other devices performed only the impacting function. These devices did not attach to the shell and typically included a shaft with one end for receiving an impact and another end for delivering the impact to the shell. With these devices, misalignment during the impacting process was likely.

The cup positioning impactor device by Ostieonics could be used to perform both the shell holding and impacting functions. This device loosely engaged a set of holes on the face of the insert and shell assembly and, could itself be used to impact the shell. Although this device did provide some angular support for aligning the shell, it provided no positive engaging means for axially aligning the shell.

Similarly, the acetabular cup positioner device by Johnson & Johnson screwed into a hole at the extreme axial center of the shell. With this device, rebound during the impacting process tended to pull the shell out of the opening. Additionally, when the device was unscrewed from the shell, the shell could twist or tilt in the opening and misalign.

SUMMARY OF THE INVENTION

It is a general object of the invention to provide an apparatus and method adapted to overcome the above described problems and others associated with installing the prosthetic socket shell or implants during total joint replacement surgery for a ball-and-socket type joint structure. More particularly, it is an object of the invention to provide a prosthetic socket implant installing device for holding and properly aligning a prosthetic implant and then impacting the implant to properly seat it in a prepared bone structure opening.

In order to accomplish these objects, a modular installation tool embodying the principles of the invention includes unique holding, aligning, and impacting mechanisms for installing a prosthetic socket implant. The elongated installation tool includes a tool body, engaging means for engaging or gripping a groove around the rim of a socket implant, and engagement control means for retracting and extending the engaging means and allowing the engaging means to securely engage or grip implants in a wide size range. An impacting rod is also preferably included in the installation tool for impacting the prosthetic socket implant separately from the holding function and without losing alignment control.

The engaging means preferably includes a plurality of engaging or gripping fingers for engaging the a rim groove or other feature on the implant around its internal or external circumference, each finger is pivotally connected to the tool body so that it may extend and retract. Engagement control means preferably includes a spring loaded mechanism that continually applies an engagement force to each engaging finger to extend the fingers to an extended, implant engaging position. The engagement control means also preferably includes a releasing mechanism for enabling the user to overcome the force applied by the spring loaded mechanism, thereby enabling the engaging fingers to retract and release the prosthetic socket implant. Also, a locking mechanism is associated with the tool body for locking the spring loaded mechanism in place to positively lock the implant engaging fingers in an engaged position holding a socket implant.

The installation tool according to the invention also preferably includes alignment means that provides both axial and angular references for the surgeon. The preferred alignment means includes indicia on one of the engaging fingers for aligning with a reference feature on the implant and allowing the holding tool to provide an angular reference to the surgeon during the shell installation. Additionally, the alignment means may also include abduction and anteversion indicating bars connected to the tool body for providing an axial alignment guide for the surgeon.

The impacting rod is slideably mounted within an opening extending along the longitudinal axis of the tool body. Because the impacting rod is radially captured and axially isolated from the tool body, and be, cause it delivers a blow to the implant precisely along the longitudinal axis of the tool body, the impacting rod according to the invention reduces the possibility of misalignment during impaction.

The present invention also includes a method for installing a prosthetic socket implant. The method of installing the implant includes engaging or gripping a feature inside the implant with the installation tool engaging fingers and then securing the implant in the patient with the implant held securely on the installation tool. Further steps include aligning the implant on the installation tool with the angular alignment indicia and aligning the implant in the prepared pelvic opening during impaction for press fit implants.

The socket implant apparatus of the present invention provides several important advantages. The modular tool performs both holding and impacting functions, firmly engages shells of many different sizes, and can be used with both trial shells and the actual implant shells. Thus, a single tool may be used for any installation procedure regardless of the size of implant being installed or the number and size of trial shells required. The tool also provides both axial and angular references and includes alignment rods for use in hip replacement surgery that allow even inexperienced surgeons to properly align the prosthetic socket implant. Additionally, the installation tool is much faster to use than competitive products and will release the shell without disturbing this impaction or cement bond. Furthermore, the installation tool provides for easier impaction and more accurate alignment for press fit implants because the axes of the installation tool and the impacting rod align and because the impacting rod is substantially mechanically isolated from the portion of the tool holding the implant. Finally, because the installation tool provides a guide for the impacting rod, one person may impact the implant while simultaneously maintaining proper implant alignment.

These and other objects, advantages, and features of the invention will be apparent from the following description of the preferred embodiments, considered along with the accompanying drawings.

DESCRIPTION OF THE PREFERRED EMBODIMENTS

FIGS. 1 through 5 illustrate a prosthetic socket implant installation tool 10 embodying the principles of the present invention. The tool 10 is intended particularly for use in installing an acetabular shell in the course of total hip arthroplasty. The terminology used in the following description will therefore refer particularly to the anatomical structure in and around the hip joint. However, those skilled in the art will readily appreciate that an installation device embodying the principles of the present invention may be used to install prosthetic implants in other types of joint structures, such as the shoulder joint for example.

Figure 1:
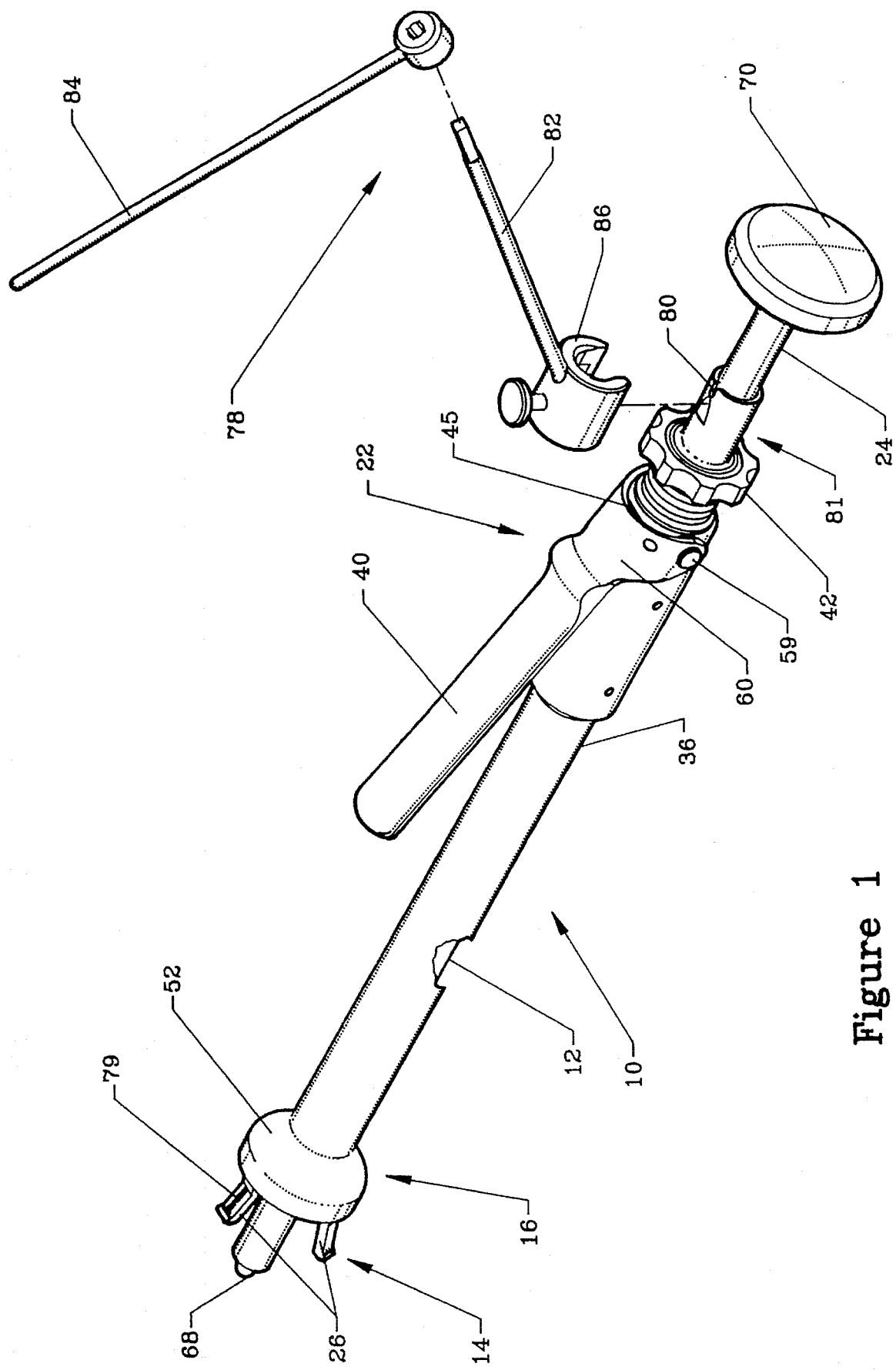
FIG. 1 is a partially exploded view in perspective illustrating a prosthetic socket implant installation tool embodying the principles of the present invention.
Figure 2:
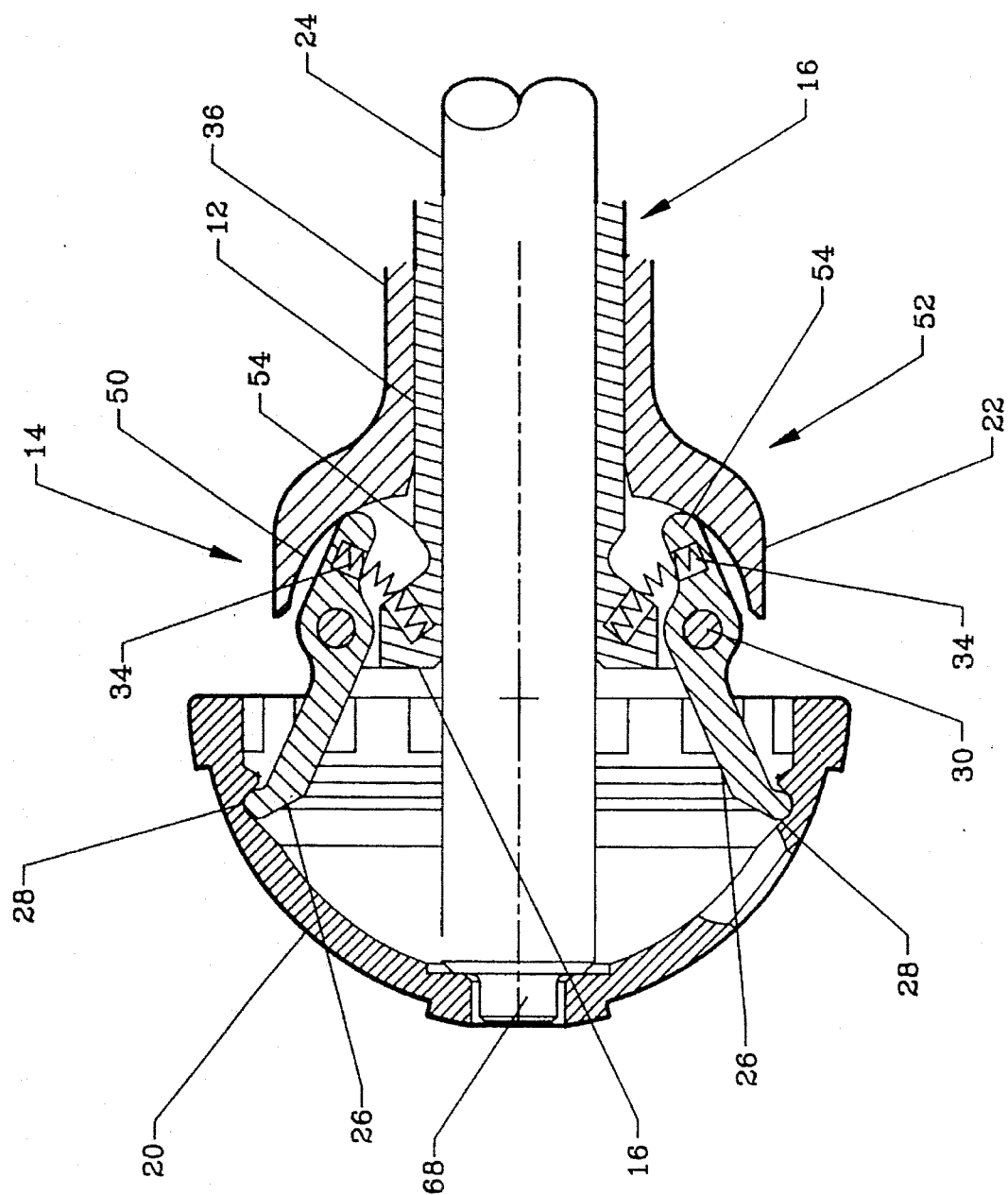
FIG. 2 is a partial longitudinal section of the tool shown in FIG. 1 with the engaging fingers in the extended position engaging a socket implant.

Referring to FIGS. 1 and 2, the preferred socket implant installation tool 10 comprises an elongated tool body 12, implant engaging means 14 mounted at a first end 16 of the elongated tool body for engaging a feature around the inner rim of a socket implant 20, and engagement control means shown generally at 22. The engagement control means 22 is for retracting and extending the implant engaging means 14 allowing the implant engaging means to securely engage socket implants in a wide size range. Impacting means comprising an impacting rod 24 is also preferably included with the installation tool 10.

Figure 3:
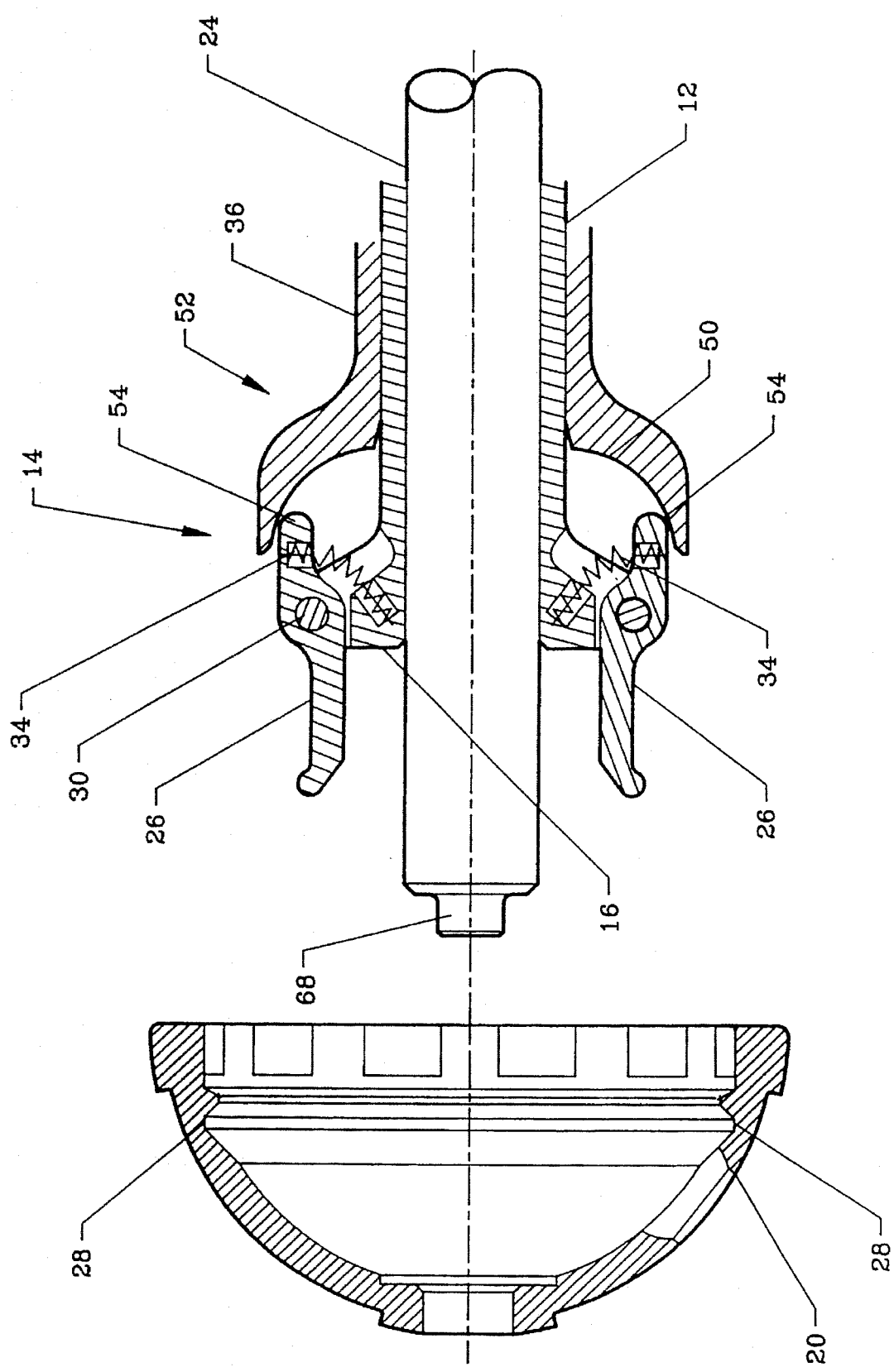
FIG. 3 is a partial longitudinal section view similar to FIG. 2 but with the engaging fingers in the retracted position.
Figure 4:
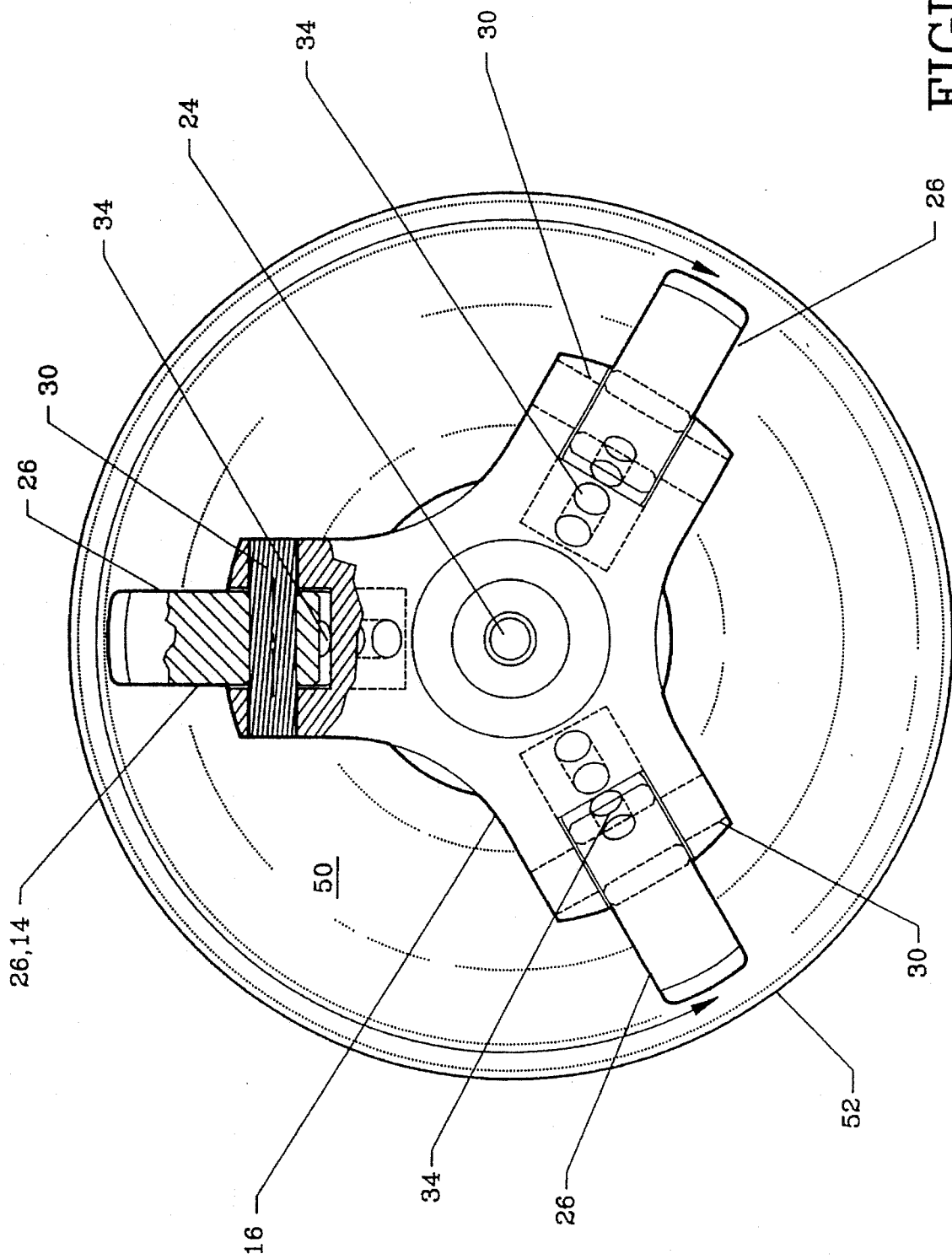
FIG. 4 is an end view of a first end of the tool shown in FIG. 1.

As shown in FIGS. 2, 3, and 4, the implant engaging means 14 preferably comprises three engaging fingers 26 for engaging a rim groove 28 on the socket implant 20 around its internal circumference. Each of the engaging fingers 26 is connected to the first end 16 of the elongated tool body 12 with a suitable pivot connection 30. Retracting springs 34 continually apply force to each engaging finger 26, forcing the fingers 26 towards a retracted position shown in FIG. 3.

Figure 5:
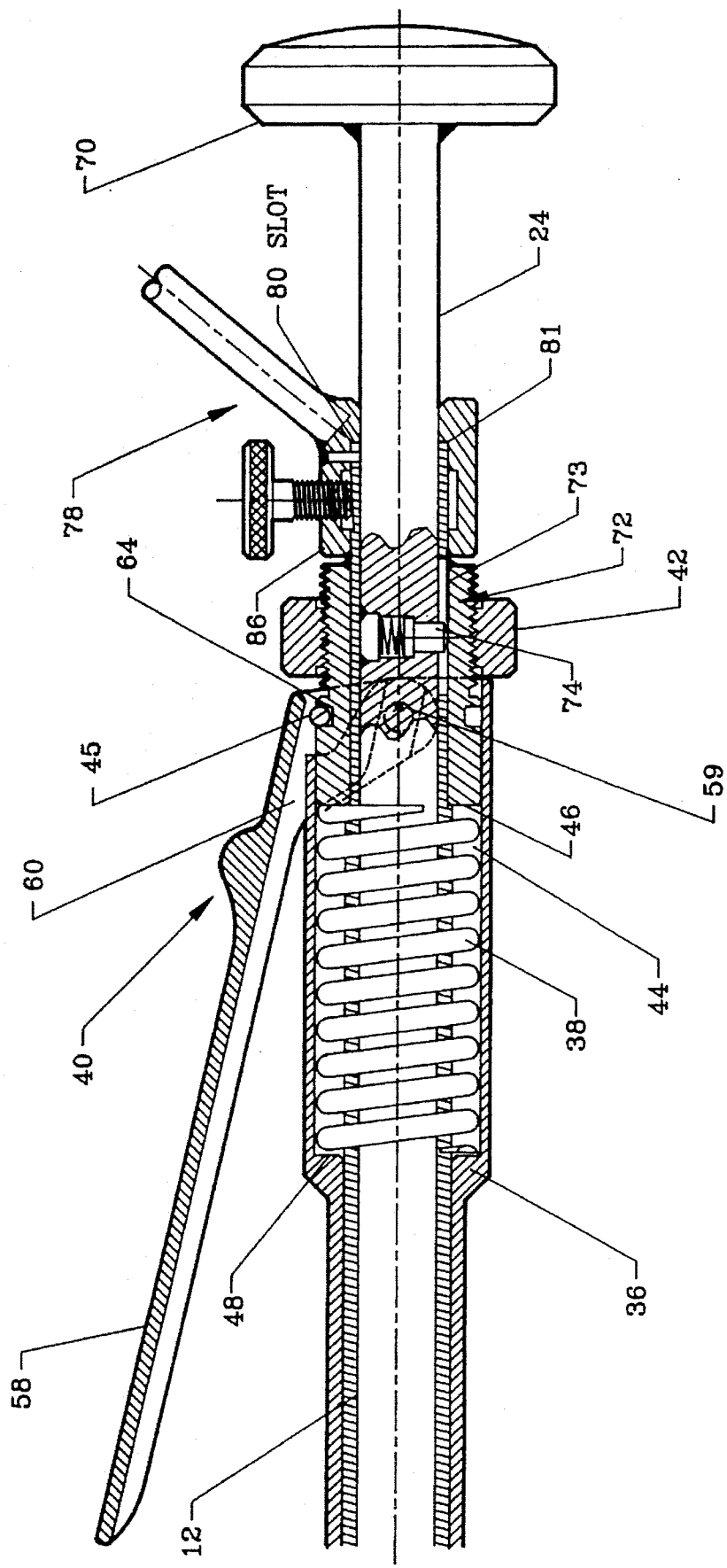
FIG. 5 is a partial transverse section of the tool shown in FIG. 1 showing a portion of the engagement control means.

Engagement control means 22 preferably includes a hollow elongated outer body 36 in which the elongated tool body 12 is slideably mounted, and extension biasing means comprising spring 38 for applying an extension biasing force between the elongated tool body 12 and the hollow elongated outer body 36 as shown in FIG. 5. The extension biasing force overcomes the force provided by retracting springs 34 and biases the fingers 26 of the implant engaging means 14 to an extended position shown in FIG. 2. Release means generally shown at reference number 40 and also included in the engagement control means selectively enables the implant engaging means 14 to retract to the retracted position.

The extension biasing spring 38 is contained within an annular space 44 between the elongated hollow outer body 36 and the elongated inner body 12 and acts between an inner body stop 46 and an outer body stop 48. The extension biasing force applied by the spring 38 between inner body stop 46 and outer body stop 48 forces a curved inner surface 50 at a first end 52 of the outer body 36 into contact with a control surface 54 on each of the engaging fingers 26. As shown best in FIG. 2, the inner surface 50 presses the control surface 54 of each engaging finger 26 inwardly toward the longitudinal axis of the tool 10, pivoting the engaging fingers 26 towards the extended position. Locking nut 42 is threaded on a threaded section at a second end of the tool body 12. The threaded section extends along the length of the tool body 12 and traverses the end of the outer body 36 opposite the first end 52. The nut 42 may be threaded snuggly against the end of the outer body 36 to prevent the tool body 12 from moving relative to the outer body, and thereby fixing the engaging fingers 26 in the extended position holding an implant.

The release means 40 preferably includes a handle 58 mounted on pivots 59 on the outer body 36. The handle 58 includes, near its end hinged to the body 36, a pin 44 that fits into a groove 64 preferably extending around the circumference of the elongated inner body 12. As detailed in FIGS. 3 and 5, when the handle 58 pivots toward the hollow outer body 36, it moves the inner body stop 46 relatively closer to the outer body stop 48, compressing the spring 38. Resultantly, the first end 52 of the hollow outer body 36 moves away from the implant engaging fingers 26 allowing the retracting springs 34 to force the implant engaging fingers 26 towards the retracted position. Additionally, the handle 58 connection coupled with the axial symmetry of the tool body 12 within the outer body 36 allows the handle 58 and outer body 36 to rotate axially about the elongated tool body 12 without altering the angular alignment or extension of the implant engaging fingers 26.

The impacting rod 24 is preferably slideably mounted within an opening extending longitudinally through the elongated tool body 12. A first end 68 of the impacting rod 24 is adapted to contact the prosthetic socket implant 20 at a central point on the implant as shown in FIG. 2. A second end 70 of the impacting rod 24 includes an impacting receiving surface by which an impacting force can be transferred to the impacting rod 24 and, in turn, to the prosthetic socket implant 20 for press fit installation. Latching means 72 limits the range of movement of the impacting rod 24 slideably within the elongated tool body 12. Such latching means 72 preferably comprises a pin 74 mounted on the impacting rod 24 and a groove 73 formed in the elongated tool body 12 and prevents inadvertent separation of the impacting rod 24 from the elongated tool body 12 during use.

The installation tool 10 according to the invention also preferably includes alignment means, a portion of which is shown generally at reference number 78, for providing both axial and angular references for the surgeon. The alignment means also includes indicia 79 (FIG. 1) on one of the engaging fingers 26 for aligning with a reference feature (not shown) on the socket implant 20. A slot 80 on a second end 81 of the elongated tool body 12 is aligned with indicia 79 and, when the implant 20 is properly aligned with indicia 79, serves as a an angular reference to clock alignment means 78 during implantation.

The alignment means 78 also preferably includes an abduction indicating member 82 and an anteversion indicating member 84 connected to the elongated tool body 12 by removable connecting sleeve 86 to providing an axial alignment guide for the surgeon.

The present invention also encompasses a method for installing a prosthetic socket implant such as the implant illustrated at 20. A first step in the installation method comprises retracting to the retracted position the plurality of implant engaging fingers 26 mounted at the first end 16 of the elongated tool body 12 as shown in FIG. 3. Preferably this step includes biasing the implant engaging fingers 26 to the retracted position with the springs 34 and pivoting implant engaging fingers 26 about their respective pivotal connections 30 by compressing spring 38 with retracting means 40.

After the step of retracting the implant engaging fingers 26, the method includes the step of inserting the engaging fingers 26 into a socket opening in the prosthetic socket implant 20 while maintaining the engaging fingers 26 in the retracted position. Where angular orientation of the implant is important, such as where bone screws will help fix the implant in place, the preferred method may also include at this point aligning a reference feature (not shown) on the socket implant 20 with the implant engagement indicia 79 (FIG. 1) associated with one of the fingers on the tool body 12.

Referring particularly to FIG. 2 the method next includes the step of extending the implant engaging fingers 26 to an extended position in which the fingers 26 engage a feature such as groove 28 on the socket implant 20 around the circumference of the socket opening with an engaging force sufficient to hold the socket implant on the tool body 12. With the preferred embodiment of the installation tool 10, this finger extending step method includes the step of biasing the curved surface 50 on the elongated hollow outer body 36 into contact with a control surface 54 on each of the implant engaging fingers 26 so as to pivot the fingers to the extended position shown in FIG. 2.

After engaging the socket implant 20 with the fingers 26, the method continues with the step of securing the socket implant in an installed position in the patient while the socket implant 20 is held on the tool body 12 by the implant engaging fingers 26 in the extended position. In a press-fit installation, this securing step includes impacting the socket implant 20 to the installed position with the impacting rod 24 slideably mounted within the elongated tool body 12. In a cement installation this step requires only stabilizing the tool 10 while the cement cures.

In the case of hip arthroplasty, three additional steps provide correct axial and angular alignment to place the socket implant 20 in the desired installed position. The first step is to position the patient on his or her side on a table with a planar table surface so that the patient's spine is substantially parallel to the table surface and so the patient's pelvis is substantially perpendicular to the table's surface with the hip joint to be replaced facing away from the table. Next are the steps of aligning the abduction bar 82 so that it is generally perpendicular to the table surface and the anteversion bar 84 so that it is generally parallel with the patient's spine.

Once the implant 20 is in the installed position, the method concludes with the steps of retracting the implant engaging fingers 26 to the retracted position and then withdrawing the engaging fingers from the socket opening while the implant engaging fingers 26 are in the retracted position. These final steps of retracting and withdrawing the fingers 26, place substantially no force on the socket implant 20 and therefore pose no risk of displacing the implant either angularly or axially from the desired installed position.

The above described preferred embodiments are intended to illustrate the principles of the invention, but not to limit the scope of the invention. Various other embodiments and modifications to these preferred embodiments may be made by those skilled in the art without departing from the scope of the following claims.

We claim:

1. A prosthetic socket implant installation apparatus comprising:
   (a) an elongated tool body;
   (b) a hollow elongated outer body in which the tool body is slideably mounted;
   (c) implant engaging means connected to the tool body at a first end of the tool body and being movable between an extended position and a retracted position, the implant engaging means for engaging a feature on a socket implant at a plurality of positions spaced out around a circumference of the socket implant when in the extended position;
   (d) an extension biasing spring applying an extension biasing force between the tool body and the outer body for biasing the tool body to a first position relative to the outer body, in which first position the implant engaging means is moved to the extended position by contact between the outer body and the implant engaging means at the first end of the tool body;
   (e) release means operable to overcome the extension biasing force applied by the extension biasing spring for selectively enabling the implant engaging means to retract to the retracted position;
   (f) a threaded section formed on the tool body at a second end thereof, the threaded section extending out of the outer body; and
   (g) a lock nut threaded on the threaded section of the tool body extending out of the outer body, the lock nut in position to be threaded snugly against an end of the outer body in locked position in which the contact between the lock nut and the outer body prevents the tool body from moving from the first position relative to the outer body.

2. The apparatus of claim 1 further comprising:
   (a) alignment means connected to the tool body for facilitating the proper alignment of the socket implant during its placement in a patient.

3. The apparatus of claim 2 wherein the alignment means comprises:
   (a) implant engagement indicia located on the implant engaging means;
   (b) an abduction indicating member connected to the tool body; and
   (c) an anteversion indicating member connected to the tool body.

4. The apparatus of claim 1 wherein the implant engaging means comprises:
   (a) at least three elongated engaging fingers spaced out around the transverse periphery of the tool body, each engaging finger being pivotally connected to the tool body.

5. The apparatus of claim 1 wherein the elongated tool body has an opening extending longitudinally therethrough along a tool body longitudinal center axis, and further comprising:
   (a) an impacting member mounted within the longitudinal opening through the tool body so that it may move longitudinally with respect to the tool body and implant engaging means to an impacting position in which the impacting member contacts a socket implant engaged by the implant engaging means to impart an impact directly to said socket implant.

6. A prosthetic socket implant installation apparatus comprising:
   (a) an elongated tool body;
   (b) implant engaging means mounted at a first end of the elongated tool body and being moveable between an extended position and a retracted position, the implant engaging means for engaging a feature on a socket implant at a plurality of positions spaced out around a circumference of the socket implant when in the extended position;
   (c) engagement control means associated with the tool body for extending the implant engaging means to the extended position and for selectively enabling the implant engaging means to retract to the retracted position;
   (d) impacting means mounted on the elongated tool body so as to be moveable along a longitudinal axis of the tool body for moving to an impacting position in which the impacting means directly contacts a center of an implant engaged by the implant engaging means to apply an impact directly to said implant while the implant engaging means is in the extended position engaging said implant; and (e) locking means for maintaining the implant engaging means in the extended position.

7. The apparatus of claim 6 wherein:

(a) the tool body includes an opening extending longitudinally therethrough along a longitudinal center axis of the tool body; and (b) the impacting means comprises an impacting member mounted within the longitudinal opening through the tool body so as to be longitudinally slideable through the longitudinal opening.

* * * * *